United States Patent
Peters et al.

(10) Patent No.: US 7,371,724 B2
(45) Date of Patent: May 13, 2008

(54) KAPREKY PEPTIDOMIMETICS AND ANALOGUES THEREOF

(75) Inventors: Carsten Peters, Vienna (AT); Christoph Buenemann, Vienna (AT); Klaus Weigand, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/449,211

(22) Filed: Jun. 8, 2006

(65) Prior Publication Data

US 2006/0281671 A1    Dec. 14, 2006

(30) Foreign Application Priority Data

Jun. 9, 2005    (GB) .................................. 0511771

(51) Int. Cl.
*A61K 38/08* (2006.01)
*A61K 38/12* (2006.01)
*C07K 7/06* (2006.01)
*C07K 7/64* (2006.01)

(52) U.S. Cl. .............................. 514/9; 514/2; 530/300; 530/317; 530/328; 530/329

(58) Field of Classification Search .................. None
See application file for complete search history.

(56) References Cited

U.S. PATENT DOCUMENTS

| 5,965,709 A | 10/1999 | Presta et al. |
| 6,777,388 B1 * | 8/2004 | Grasso et al. ................. 514/16 |
| 2002/0076420 A1 | 6/2002 | Caplan et al. |

FOREIGN PATENT DOCUMENTS

| EP | WO01/71342 | * | 9/2001 | ..................... 33/0 |
| WO | WO97/10004 | | 3/1997 | |
| WO | WO01/71342 | | 9/2001 | |

OTHER PUBLICATIONS

Nechansky et al., "Inhibition of Antigen-Induced Mediator Release from IgE-Sensitized Cells by a Monoclonal Anti-FcεRI α-Chain Receptor Antibody: Implications for the Involvement of the Membrane-Proximal α-Chain Region in FcεRI-Mediated Cell Activation," J Immunol, vol. 166, pp. 5979-5990 (2001).

* cited by examiner

*Primary Examiner*—Anish Gupta
*Assistant Examiner*—Julie Ha

(57) ABSTRACT

Analogues of the amino acid sequence KAPREKY and their use in screening for compounds which interacts with FcεRIα.

3 Claims, No Drawings

KAPREKY PEPTIDOMIMETICS AND ANALOGUES THEREOF

The present invention relates to organic compounds, such as KAPREKY peptidomimetics.

Activation of mast cells and basophils is triggered by the binding of IgE to the a-chain (FcεRIα) of the high affinity IgE-receptor followed by cross-linking with polyvalent antigen, see e.g. M. J. Nadler et al, Adv. Immunol. 2000, 76, 325-355. This leads to degranulation and the release of preformed mediators (e.g. histamine, tryptase and others) and to the synthesis of chemokines and cytokines as well as prostaglandins and leukotrienes. These molecules in turn modulate inflammatory cell activation and recruitment, vascular leakage, smooth muscle contraction, and mucus secretion associated with allergic reaction. It was shown previously that an anti-human FcεRIα-monoclonal antibody (5H5/F8) which recognizes the human FcεRIα-specific, membrane-proximal epitope 171KAPREKY177 is able to inhibit the IgE-induced mediator release without affecting the binding of IgE to the same receptor, see e.g. A. Nechansky et al, *J. Immunol.* 2001, 166, 5979-5990 and the KAPREKY epitope thus represents a molecular target for the modulation of FcεRIα-mediated cell activation. E.g. in WO0171342 is disclosed that the amino acid sequence of the peptide (KA)PREKY(WYL) may be used in a method for the identification of agents that interfere with cell activation induced via FcεRIα, e.g. as a molecular target in a screening assay. A compound (ligand) which binds to the amino acid sequence (KA)PREKY(WYL) may—in homology to mAb 5H5F8—inhibit allergen induced sulfidoleukotriene release from IgE sensitized human pheripherial blood leukocytes. In consequence, such an identified compound (agent) may interfere with the signal transduction cascade responsible for cell activation after crosslinkage of FcεRIα bound human IgE. Compounds identified by such a screening assay, e.g. a pharmaceutical composition comprising such identified compound beside pharmaceutically acceptable carriers or diluents, in consequence may be useful in the inhibition of mast cell/basophil activation involved in allergic response, which e.g. is connected with atopic diseases. A ligand identified according to WO0171342 may thus be useful e.g. in the treatment of allergic asthma, allergic rhinitis, atopic dermatitis and chronic urticaria mediated by auto-antibodies directed against IgE or FcεRIα.

We have now found novel molecular targets which are useful in screening for the identification of a ligand that interferes with cell activation induced via FcεRIα.

In one aspect the present invention provides an KAPREKY-analogue, such as a conformationally constrained KAPREKY-analogue, e.g. a peptidomimetic of KAPREKY, such as a compound which mimics the putative 3D structure of the peptide KAPREKY, e.g. which peptide KAPREKY is present in FcεRIα.

KAPREKY. SEQUENCE ID NO. 1, as used herein includes the peptide having the amino acid sequence KAPREKY, SEQUENCE ID NO. 1, and a peptide containing the amino acid sequence of the peptide KAPREKY, SEQUENCE ID NO. 1, e.g. as a part of the whole sequence, e.g. a peptide of the amino acid sequence NITVIKAPREKY, SEQUENCE ID NO. 2, ESEPLNITVIKAPREKYWL, SEQUENCE ID NO. 3, and KAPREKYWL, SEQUENCE ID NO. 4.

KAPREKYWL in FcεRIα has a chemical structure of formula

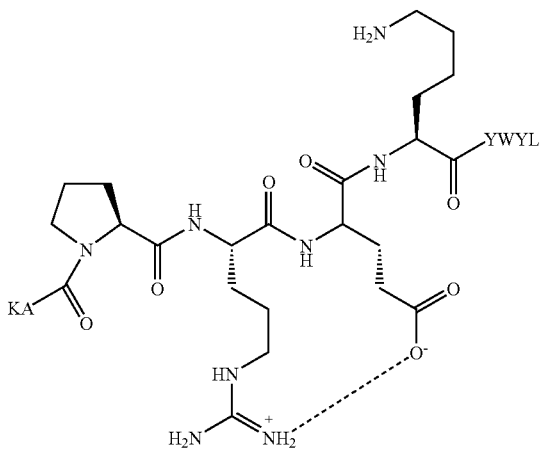

wherein K, A, Y, W, Y and L are the amino acid residues K, A, Y, W and L as used in peptide terminology.

From an X-ray structure of the 5H5/F8 Fab-fragment in complex with the KAPREKY peptide the existence of a distinct secondary structure is known that is stabilized by internal hydrogens bonds. A loop of the peptide which is stabilized by a salt bridge between Arg(4) and Glu(5) seems to offer a major contribution to the buried surface of the peptide-antibody complex.

Our design of conformationally constrained peptides that mimic the putative conformation of the KAPREKY amino acid sequence comprises two approaches A) Modification of the peptide backbone, e.g. by substitution of Arg(4) or Glu(5) with rigid, non-natural mimics or by introduction of a cyclic backbone. A special way of rigidifying the backbone is the linkage between neighboring amino acids, e.g. by introduction of modified Hyp instead of Pro, e.g. to obtain a compound of formula

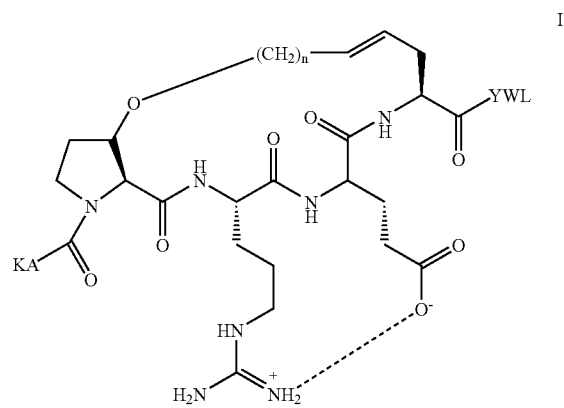

wherein K, A, Y, W, L and $R_2$ are as defined above and n is a number selected from 1 to 6, such as 1 to 4, or to obtain a compound of formula

II

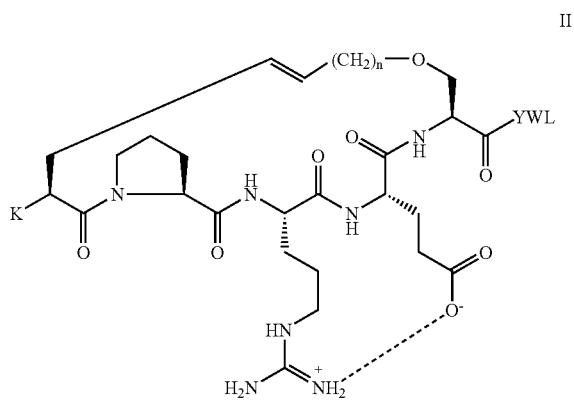

wherein K, Y, W, and L are as defined above, or to obtain a compound of formula

III

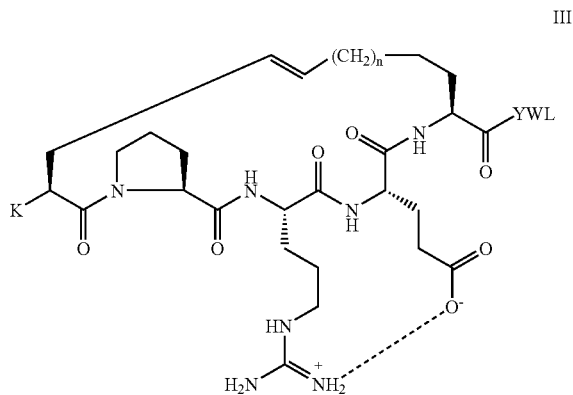

wherein K, Y, W and L are as defined above,

B) Stabilization of the Arg-Glu side chain interaction by a covalent bond. This we achieve by introducing an aminoguanindine moiety at the Arg residue by creating a cyclic tripeptide that contains an glycine-bridge, e.g. to obtain a compound of formula

IV

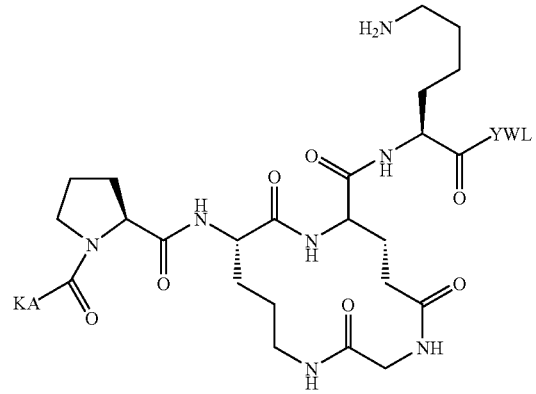

or to obtain a compound of formula

V

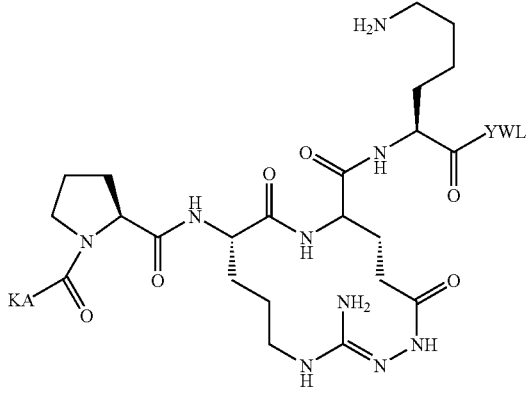

In another aspect the present invention provides KAPREKY-analogue of formula I, II, III, IV or V.

A KAPREKY analogue may be prepared as appropriate, e.g. according, e.g. analogously, to a method as conventional.

In one preferred embodiment of the present invention a KAPREKY-analogue, e.g. of formula IV may be prepared according to the following REACTION SCHEME 1:

REACTION SCHEME 1

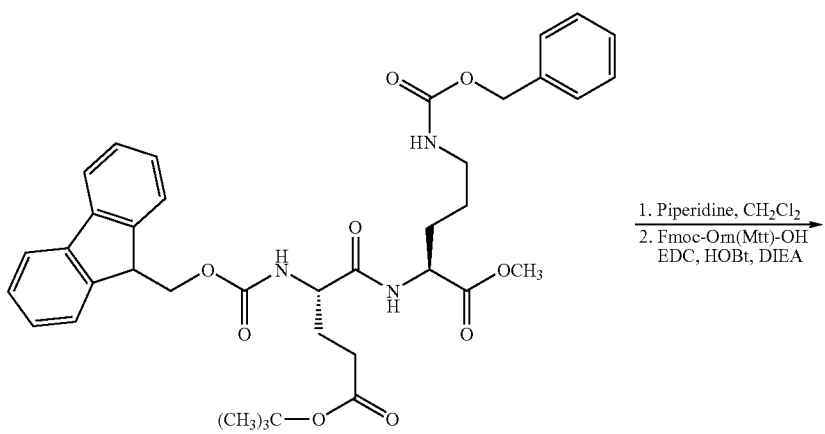

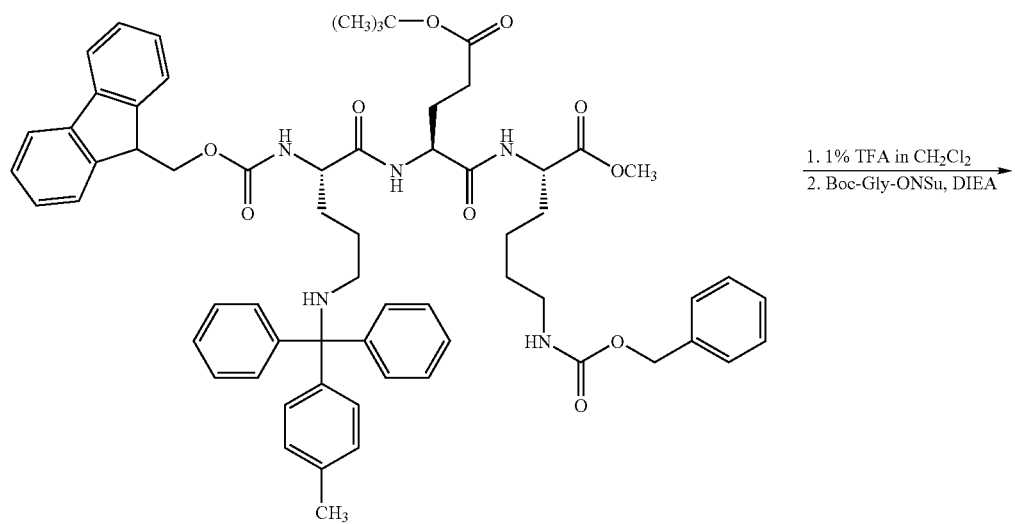
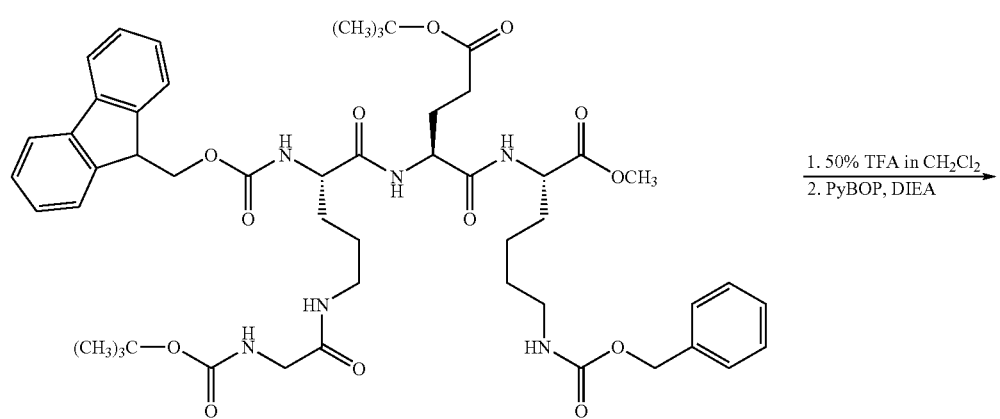
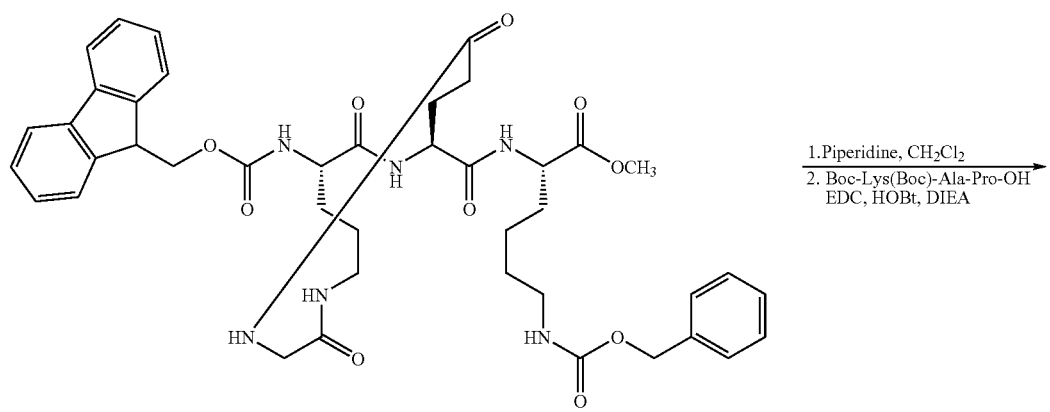
IIIA

-continued

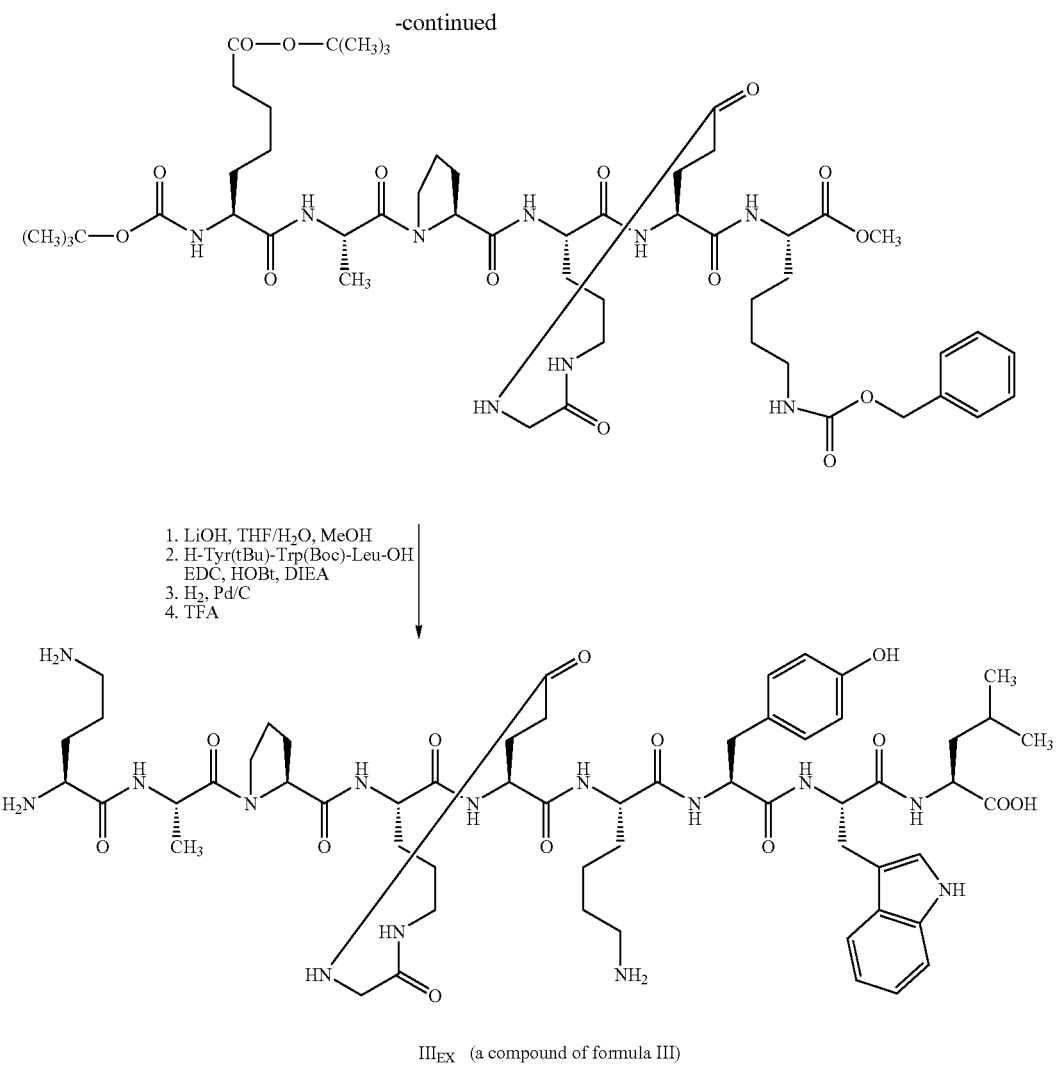

III$_{EX}$ (a compound of formula III)

The glycine-bridged peptidomimic of formula III may be synthesized by means of standard peptide chemistry. The cyclization step which results in a compound of formula IIIA is carried out under high-dilution conditions. After successful cyclization the resulting compound of formula IIIA is elongated in N-terminal direction and then completed by C-terminal elongation. A modified KAPREKYWL peptide of formula III$_{EX}$ which is a compound of formula III is obtained.

In another preferred embodiment of the present invention a KAPREKY-analogue, e.g. a compound of formula I, may be prepared according to the following REACTION SCHEME 2:

REACTION SCHEME 2

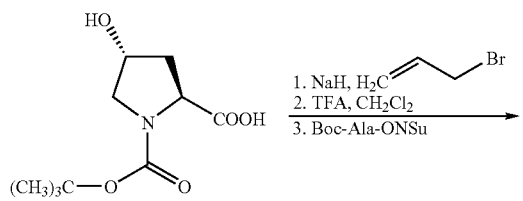

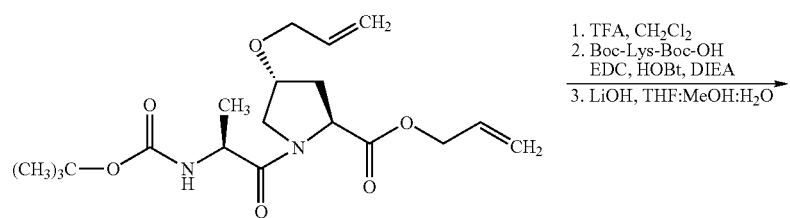
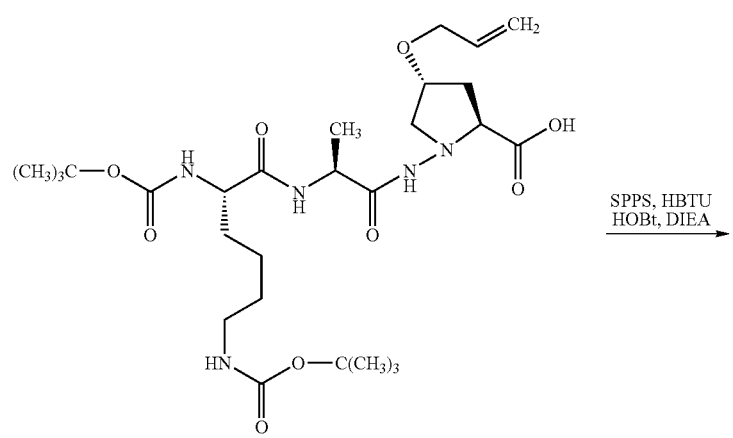
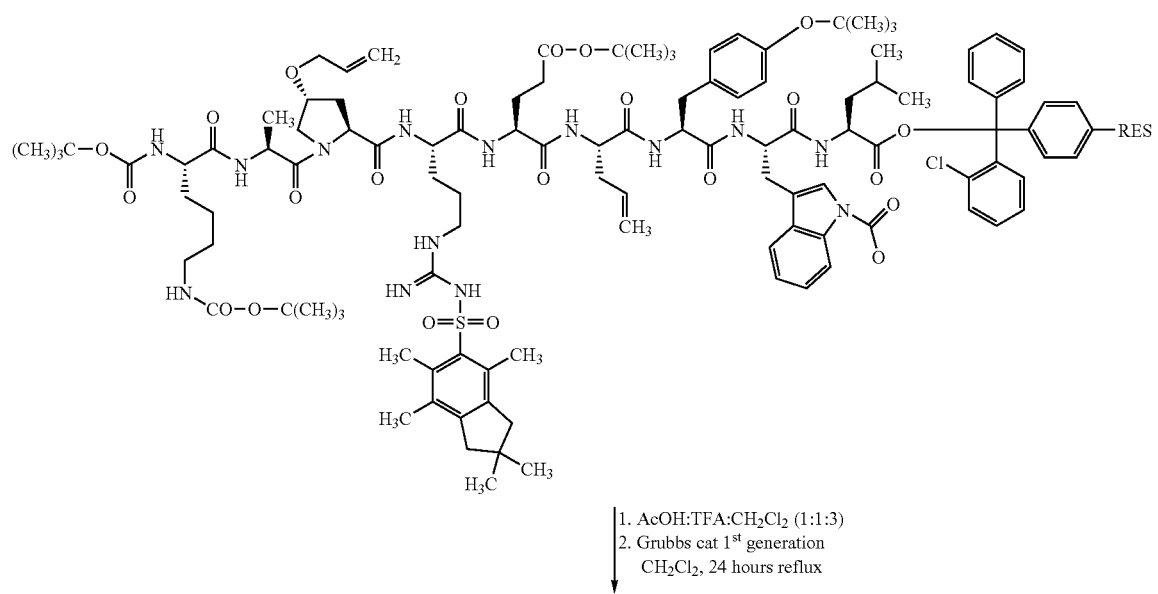

-continued
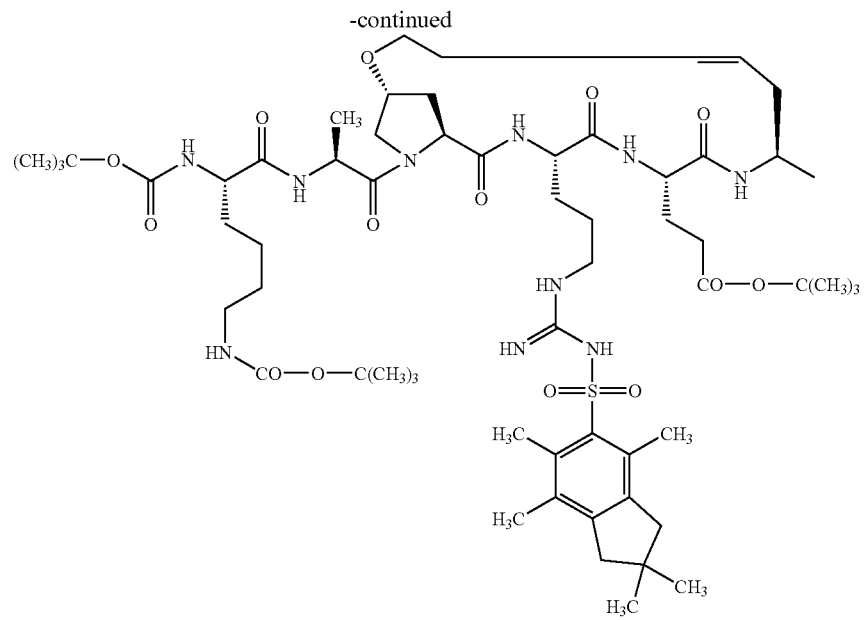
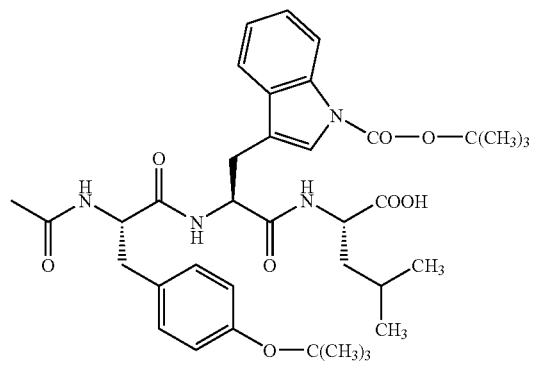
TFA:TIS:H₂O
95:2.5:2.5
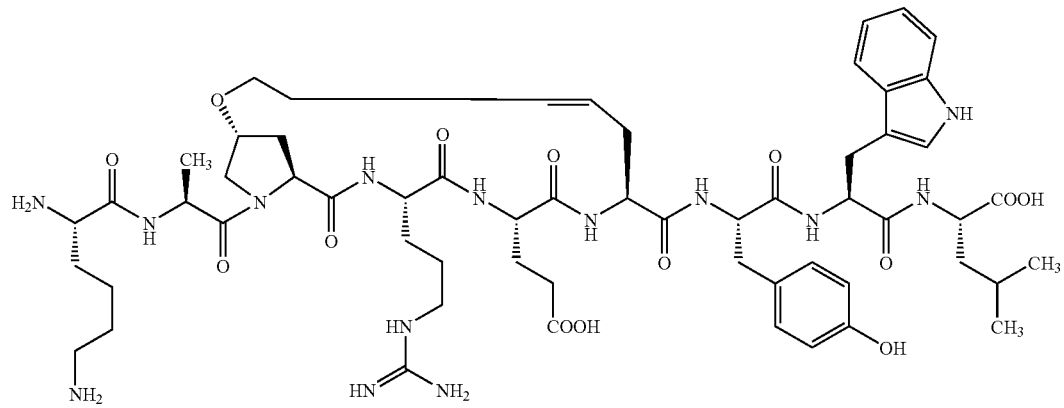
I_EX  (a compound of formula I)

In REACTION SCHEME 2 "RES" is a solid support (a resin), and Grubbs cat is a Grubb's catalyst 1$^{st}$ generation, i.e. a compound of formula

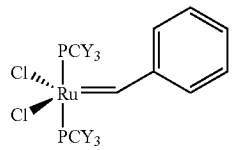

wherein "PCy$_3$" is tricyclohexylphosphinebenzylidine.

The synthesis of peptidomimetics of formula II and III, respectively, are carried out in an analogous manner with the incorporation of the appropriate building blocks during SPPS. For the synthesis of the backbone-constrained peptidomimetic according to REACTION SCHEME 2 a convergent approach is chosen that consists of a combination of solution- and solid-phase chemistry. Firstly, a tripeptide containing an allyl-modified hydroxyproline is synthesized in solution (see first two steps in REACTION SCHEME 2). This peptide is coupled to a polymer-bound hexapeptide that had been synthesized before by means of Fmoc-SPPS (wherein the polymer is a solid support), see third step in REACTION SCHEME 2. The solid phase synthesis is achieved using 2-chlorotrityl-linkage that allows cleavage of the fully protected nonapeptide under mild conditions. The resulting peptide is subjected to ring-closing metathesis-reaction using a first generation Grubbs-Catalyst according to the fourth step in REACTION SCHEME 2, in which step mostly E-isomer is formed according to H-NMR analysis. In the last step final deprotection is carried out by treatment with acid to yield a compound of formula $I_{EX}$, which is a compound of formula I.

KAPREKY-analogues provided by the present invention are hereinafter designated as "compound(s) of (according to) the present invention". A KAPREKY-analogue includes a compound of formula I, of formula $I_{EX}$, of formula II, of formula III, of formula $III_{EX}$ and of formula IV. A compound of the present invention includes a compound in any form, e.g. in free form, in the form of a salt, in the form of a solvate and in the form of a salt and a solvate.

In another aspect the present invention provides a compound of the present invention in the form of a salt.

A salt of a compound of the present invention includes a metal salt or an acid addition salt. Metal salts include for example alkali or earth alkali salts; acid addition salts include salts of a compound of formula I with an acid, e.g. hydrogen fumaric acid, fumaric acid, naphthalin-1,5-sulphonic acid, hydrochloric acid, deuterochloric acid; trifluoroacetic acid, preferably hydrochloric acid, trifluoroacetic acid.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of of the present invention may exist in the form of isomers and mixtures thereof; e.g. optical isomers, diastereoisomers, cis/trans conformers. A compound of the present invention may e.g. contain asymmetric carbon atoms and may thus exist in the form of enatiomers or diastereoisomers and mixtures thereof, e.g. racemates. Any asymmetric carbon atom may be present in the (R)-, (S)- or (R,S)-configuration, preferably in the (R)- or (S)-configuration. For example, in the backbone of KAPREKY-analogues there are several asymmetric C-atoms and substituents attached to such asymmetric C-atoms (indicated in KAPREKY-analogue formulae by dotted lines or bold bonds) may be in the (R)-, (S)- or (R,S)-configuration. Preferably such substituents are in the same configuration as in the KAPREKY part of human FcεRIα (where applicable). Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of formula I, where tautomers can exist.

Compounds of the present invention are as a molecular target e.g. useful for screening for compounds which interact with the sequence of a KAPREKY-analogue of the present invention (e.g. in homology to KAPREKY) and in consequence which interact with FcεRIα, e.g. human FcεRIα. Interaction between an KAPREKY-analogue and a screening-compound includes the binding of the screeening-compound to the sequence of an KAPREKY-analogue.

Such screening may be carried out as appropriate, e.g. by screening in solution and determining effects by an appropriate method, such as an NMR method, e.g. by screening within a lipid environment resembling the cell surface and determining effects by an appropriate method, e.g. by fluorescence spectroscopy on vesicles. Such interaction may be determined in screening assays, e.g. in High Trough Put screening assays, e.g. in the form of a kit.

In another aspect the present invention provides a kit for identifying an agent which interacts with a compound of the present invention which kit comprises as a main component a compound according to the present invention.

Such kit may further comprise a substantial component such as
means for a contact with a candidate LMW-binder;
means for determining the effect of the candidate LMW-binder on a compound of the present invention,
an appropriate environment for using such means.

In another aspect the present invention provides a method of identfying an agent which interacts with a compound of the present invention e.g. a method of identifying an agent which interacts with FcεRIα, e.g. in homology to KAPREKY(WYL), which method comprises
A) contacting a compound of the present invention with a candidate compound,
B) determining the effect of the candidate compound on a compound of the present invention,
C) choosing a candidate compound from which an effect has been determined in step B).

A compound which interacts with, e.g. which binds to, a compound of the present invention, is herein also designated as "agent(s) of (according to) the present invention". An "agent" as used herein includes an agonist or an antagonist, preferably an antagonist (inhibitor) of FcεRIα. An (ant)agonist is a candidate compound from which an effect on FcεRIα has been found in a screening assay or in a method for identifying (ant)agonists according to the present invention. An (ant)agonist may decrease or enhance the production and or the biological activity of FcεRIα.

A candidate compound includes peptides, peptidomimetics, antibodies, including monoclonal and polyclonal antibodies, fragments of antibodies or chemical entities, e.g. LMW (low molecular weight) compounds, e.g. in the form of compound libraries, from which the effect on a compound of the present invention is unknown. An agent includes a candidate compound from which an effect has been determined.

Agents of the present invention identified by a method of the present invention may be useful compounds interacting with FcεRIα and for determining effects on FcεRIα.

In another aspect the present invention provides the use of a compound of the present invention and the use of a kit of the present invention for identifying an agent which interacts with FcεRIα.

In another aspect the present invention provides an agent which interacts with FcεRIα, preferably an antagonist, which is characterized in that said agent can be provided by the following method steps:
A) contacting a compound of the present invention with a candidate compound,
B) determining the effect of the candidate compound on a compound of the present invention,
C) choosing a candidate compound from which an effect has been determined in step B).

A screening assay may be e.g. provided as follows:

A compound of the present invention is immobilized onto a surface, e.g. a plastic surface, creating a selection matrix for potential ligands. Candidate compounds may be provided as appropriate, e.g. by a method as conventional, e.g by provision of libraries, e.g. phage libraries which display random peptides of various lenghts (Devlin et al, 1990, Science 249: 404-406; Cortese et al., 1995, Curr. Opin. Biotech. 6: 73-80) or random peptide libraries displayed on the flagella of *Escherichia coli* (Lu et al., 1995, Biotechnology 13: 366-372). After enrichment of specifically binding clones by several rounds of panning against the selection matrix, binding clones are isolated and the amino acid sequence of the peptides displayed by these clones are determined by translation of the encoding DNA sequence. The identified amino acid sequences may serve as templates for the synthesis of peptides which can be tested.

Test methods which ascertain the binding of an agent to FcεRIα or the capability of a peptide which inhibits allergen induced mediator release from IgE sensitized cells are known or may be carried out as appropriate.

Other canditate compounds may comprise combinatorial libraries e.g. immobilized on beads. Beads that contain substances that bind to the amino acid sequence of a compound of the present invention which is immobilized onto a surface can be identified e.g. by confocal nanomicroscopy which is an established well known method. The bead can be picked specifically and the immobilized compound can be cleaved off and identified; e.g. by nuclear magnetic resonance analysis.

An agent identified by a method of the present invention, e.g. an antagonist, may be useful
for inhibition of allergen induced sulfidoleukotriene release from IgE sensitized human pheripherial blood leukocytes,
for interfering with the signal transduction cascade responsible for cell activation after crosslinkage of FcεRIα bound human IgE,
for the inhibition of mast cell/basophil activation; and consequently
for the treatment of diseases,
such as allergic diseases, e.g. including urticaria, e.g. chronic urticaria; allergic reactions to medication; rhinitis, e.g. allergic rhinitis; conjunctivitis, e.g. rhinoconjunctivitis; dermatitis, e.g. atopic dermatitis; asthma, e.g. atopic asthma and allergic asthma; anaphylactic shock; preferably atopic dermatitis, allergic asthma, allergic rhinitis, allergic rhinoconjunctivitis, and chronic urticaria, such as allergic asthma or atopic dermatitis, e.g. diseases mediated by auto-antibodies directed against IgE or FcεRIα.

An agent according to the present invention may thus be useful as a pharmaceutical.

In another aspect the present invention provides
an agent of a compound of the present invention, e.g. in the form of a pharmaceutical composition, for use as a pharmaceutical,
a pharmaceutical composition comprising an agent identified by a method of the present invention beside pharmaceutically acceptable excipient.

In another aspect the present invention provides
a method for inhibiting mast cell/basophil activation,
a method for inhibition of allergen induced sulfidoleukotriene release from IgE sensitized human pheripherial blood leukocytes,
a method for interfering with the signal transduction cascade responsible for cell activation after crosslinkage of FcεRIα bound human IgE,
a method for the inhibition of mast cell/basophil activation; and
a method of treating diseases, such as allergic diseases, e.g. including urticaria, e.g. chronic urticaria; allergic reactions to medication; rhinitis, e.g. allergic rhinitis; conjunctivitis, e.g. rhinoconjunctivitis; dermatitis, e.g. atopic dermatitis; asthma, e.g. atopic asthma and allergic asthma; anaphylactic shock; preferably atopic dermatitis, allergic asthma, allergic rhinitis, allergic rhinoconjunctivitis, and chronic urticaria, such as allergic asthma or atopic dermatitis, e.g. diseases mediated by auto-antibodies directed against IgE or FcεRIα. comprising administering an effective amount of an agent of the present invention to a subject in need of such treatment.

In another aspect the present invention provides the use of an agent identified by a method of the present invention for the preparation of a medicament for use in
mast cell/basophil activation,
in inhibition of allergen induced sulfidoleukotriene release from IgE sensitized human pheripherial blood leukocytes,
in interfering with the signal transduction cascade responsible for cell activation after crosslinkage of FcεRIα bound human IgE,
in the inhibition of mast cell/basophil activation; and
in the treatment of allergic diseases, e.g. including urticaria, e.g. chronic urticaria; allergic reactions to medication; rhinitis, e.g. allergic rhinitis; conjunctivitis, e.g. rhinoconjunctivitis; dermatitis, e.g. atopic dermatitis; asthma, e.g. atopic asthma and allergic asthma; anaphylactic shock; preferably atopic dermatitis, allergic asthma, allergic rhinitis, allergic rhinoconjunctivitis, and chronic urticaria, such as allergic asthma or atopic dermatitis, e.g. diseases mediated by auto-antibodies directed against IgE or FcεRIα.

Treatment according to the present invention includes treatment and prevention.

In another aspect the present invention provides a method for identifying an FcεRIα agent that interfere with allergen induced and FcεRIα mediated cell activation comprising providing a selection matrix comprising the amino acid sequence of an KAPREKY-analogue according to the present invention in a fluid environment in the presence of a candidate compound, determining whether said candidate compound binds to said selection matrix and identifying a candidate compound which binds to said selection matrix and isolating the agent which binds to said selection matrix.

In the following Examples all temperatures are in ° Celsius and are uncorrected. The following abbreviations are used in the description and in the Examples:

AcOH acetic acid
ALL allyl
Boc: t.butyloxycarbonyl
DIEA: diisopropylethylamine
EDC*HCl (1-ethyl-3-[3-dimethylaminopropyl]carbodiimide hydrochloride salt
Fmoc a group of formula

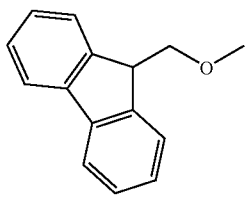

HBTU is a coupling reagent, i.e. a compound of formula

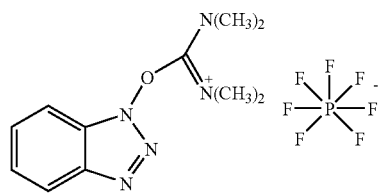

HOBt is a coupling reagent, i.e. a compound of formula

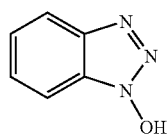

MeOH methanol
min minutes
MNP N-methylpyrrolidone
Mtt the group 4-methyl-triphenylmethyl
Pbf: the group 2,2,4,6,7-pentamethyldihydrobenzofurane-5-sulfonyl
ONSu the group N-hydroxysuccinimidyl
ByBOP benzotriazol-1-yl-oxy-tris-pyrralidino-phosponium-. hexafluorphosphate
RT: room temperature
SPPS solid-phase peptide synthesis
tBu tert.butyl
TFA: trifluoroactic acid
TIS: triisoproprylsilane
Z: the group benzyloxycarbonyl

EXAMPLE 1

SPPS for the Production of a Final Peptide (Production of Starting Material)

(See also REACTION SCHEME 2, third step)

In a typical procedure 200 mg of Leu loaded 2-chlorotrityl-resin (NovaBiochem, substitution 0.74 mmol/g)(=solid support), is treated with NMP to allow swelling of the polymer. From the mixture obained, NMP is removed and the resin is subjected to a solution of 272 mg of Fmoc-Trp (Boc)-OH [NovaBiochem], 202 mg of HBTU, 109 mg of HOBt and 153 mg of DIEA in 5 ml of NMP. The mixture obtained is stirred for 2 min at RT to allow pre-activation of the amino acid and is applied to the resin. The mixture obtained is shaken at RT for around 60 min. From the mixture obtained solvent is removed and the resin obtained is washed several times with NMP, CH$_2$Cl$_2$ and MeOH. A resin is obtained wherein the Fmoc-Trp(Boc)-OH group is bound via the oxygen of the hydroxy group.

The resin obtained is treated with a solution of 20% v/v piperidine in NMP for 2×10 min for removal of the Fmoc group and a resin is obtained wherein the tryptophane is bound to the resin in the form of OH-Trp(Boc)-O-resin. The resin obtained is washed several times with a mixture of NMP, CH$_2$Cl$_2$ and MeOH and to the resin obtained a mixture is applied which contains an Fmoc-protected amino acid which amino acid is desired to be bound to the tryptophane. This is carried out anlaogously as described above for the binding of the tryptophane resiude. That protocol as described above is repeated until the final peptide chain is built up on the resin.

The resin obtained is treated with a solution of acetic acid and trifluoroethanol in dichloromethane (1:1:3 (v/v)) for cleavage of the final peptide from the resin, from the mixture obtained the resin is filtrated off and from the filtrate obtained solvent is evaporated off to dryness. A crude final peptide is obtained and purified using RP-HPLC. Characterisation is carried out via MS and/or H-NMR. The final peptide obtained is used for ring-closing, which ring closing is carried out according to the present invention.

EXAMPLE 2

Ring-Closing Metathesis According to a Process of the Present Invention and Final Deprotection to Obtain a Compound of the Present Invention In a typical procedure 30 mg of the nonapeptide Boc-Lys (Boc)-Ala-Hyp(OAII)-Arg(Pbf)-Glu(OtBu)-Tyr(tBu)-Trp (Boc)-Leu-OH are dissolved in dry CH$_2$Cl$_2$ under argon atmosphere and to the mixture obtained 1.4 to 2.8 mg of 1$^{st}$ generation Grubbs-Catalyst are added. The resulting solution is refluxed until the starting material is disappeared (up to 24 hours). From the mixture obtained solvent is evaporated and the evaporation residue is subjected to RP-HPLC. A bridged peptide (compound of formula IA in REACTION SCHEME 2) is obtained. Characterization by MS.

The bridged peptide obtained is treated with a mixture of TFA, TIS and H$_2$O (95:2.5:2.5 (v/v)) for 3 hours at RT. The mixture (solution) obtained is cooled to 0° and treated with ice-cold diethyl ether and the deprotected bridged peptide (compound of formula I) is precipitated. The precipitate obtained isoted by centrifugation and tcharacterized by MS.

EXAMPLE 3

Production of Starting Material (Peptide Synthesis of Protected Dipeptide in REACTION SCHEME 1)

In a typical procedure 400 mg of Fmoc-Glu(OtBu)-OH*$H_2O$ is dissolved in $CH_2Cl_2$ and to the mixture obtained 152 mg of HOBt*$H_2O$ and 233 mg of DIEA are added. The mixture obtained is cooled to 0°, 190 mg EDC*HCl are added and the mixture obtainend is stirred for 30 min at 0°. To the mixture obtained 298 mg of H-Lys(Z)-OMe are added and the solution obtained is allowed to stir at 0° for 60 min and at RT for further 12 to 16 hours. The mixture obtained is subjected to aqueous workup (1 N—HCl, aqueous, saturated $NaHCO_3$-solution and brine). Optionally the protected peptide Fmoc-Glu(OtBu)-Lys(Z)-OMe obtained is subjected to purification, e.g. via chromatography on silica gel.

EXAMPLE 4

Selective Removal of Protecting Groups from Protected Amino Acids

From an Fmoc protected peptide the Fmoc-protecting group is removed by treatment with piperidine in $CH_2Cl_2$ (1:20 (v/v)) for 30 to 90 min at RT.

From an Z, or t-Bu, respectively, protected peptide the protecting group is removed by treatment of the Z-, or tBu, respectively, protected peptide with TFA/TIS in $CH_2Cl_2$ (5:0.5:4.5 (v/v)) for around 60 min at RT. Glu-Lys is obtained.

The invention claimed is:

1. A compound which is a KAPREKY-analogue in free or salt form, wherein the KAPREKY-analogue is of formula

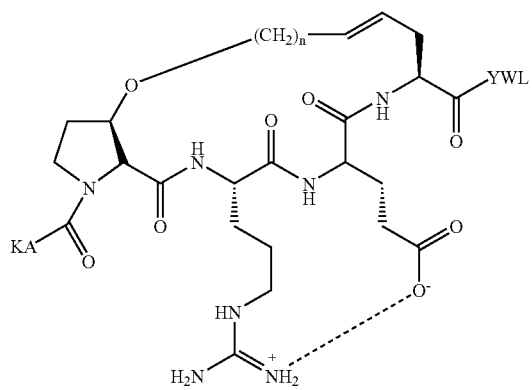

I or of formula

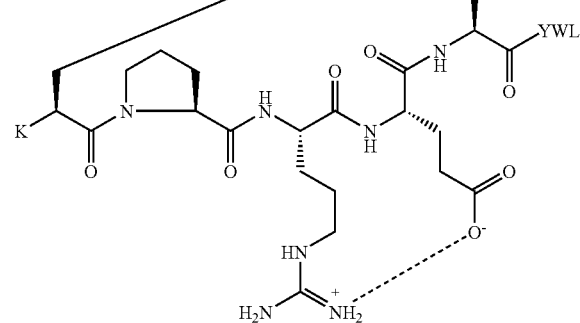

II or of formula

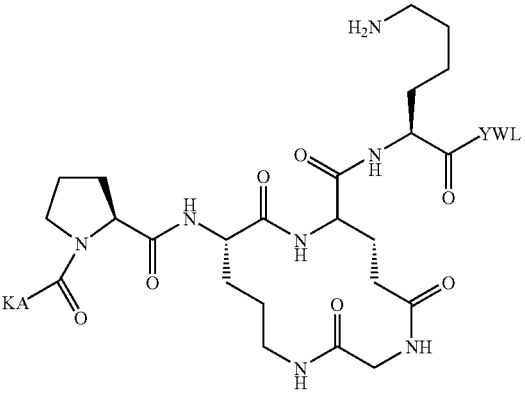

III or of formula

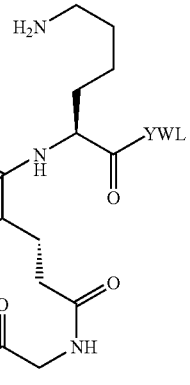

IV wherein K, A, Y, W and L are the amino acid residues K, A, Y, W and L as used in peptide terminology and n is a number selected from 1 to 4.

2. A compound according to claim 1 in free or salt form which is the compound

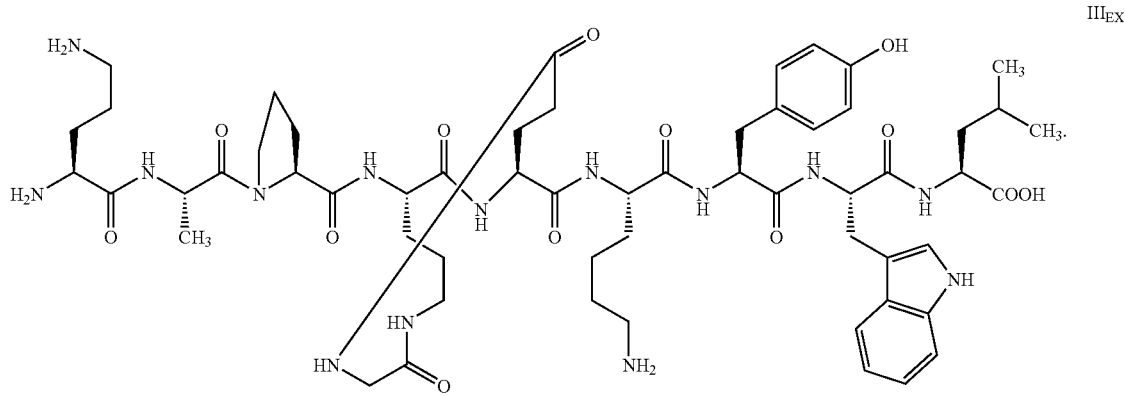

III$_{EX}$

3. A compound according to claim 1 in free or salt form which is the compound
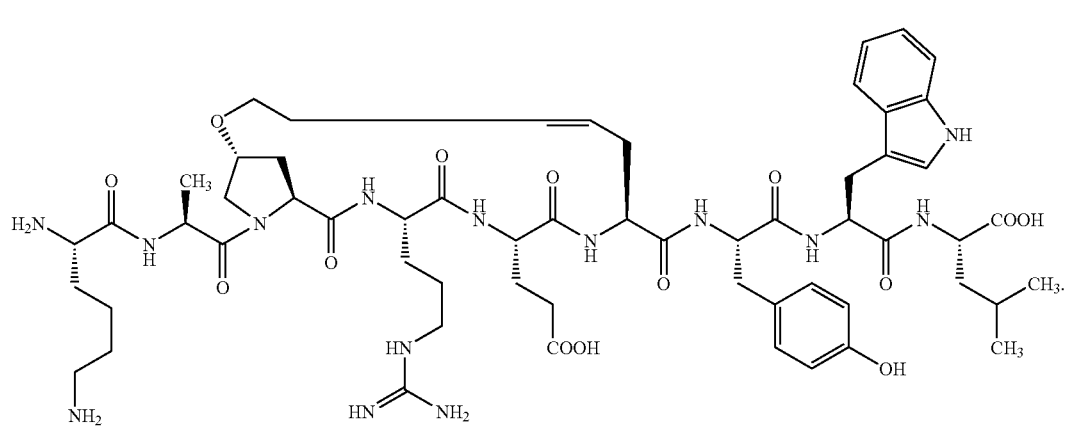
* * * * *

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: peptide within the IgE-receptor

<400> SEQUENCE: 1

Lys Ala Pro Arg Glu Lys Tyr
1               5

<210> SEQ ID NO 2
<211> LENGTH: 12
<212> TYPE: PRT
<213> ORGANISM: Artificial Sequence
<220> FEATURE:
<223> OTHER INFORMATION: peptide containing a portion of the
      IgE-receptor

<400> SEQUENCE: 2

Asn Ile Thr Val Ile Lys Ala Pro Arg Glu Lys Tyr
1               5                   10

<210> SEQ ID NO 3
<211> LENGTH: 19
<212> TYPE: PRT
<213> ORGANISM: Artificial Sequence
<220> FEATURE:
<223> OTHER INFORMATION: peptide containing a portion of the
      IgE-receptor

<400> SEQUENCE: 3

Glu Ser Glu Pro Leu Asn Ile Thr Val Ile Lys Ala Pro Arg Glu Lys
1               5                   10                  15

Tyr Trp Leu

<210> SEQ ID NO 4
<211> LENGTH: 9
<212> TYPE: PRT
<213> ORGANISM: Artificial Sequence
<220> FEATURE:
<223> OTHER INFORMATION: peptide containing a portion of the
      IgE-receptor

<400> SEQUENCE: 4

Lys Ala Pro Arg Glu Lys Tyr Trp Leu
1               5
```